United States Patent [19]

Schon

[11] Patent Number: 5,866,337

[45] Date of Patent: Feb. 2, 1999

[54] METHOD TO DETECT MUTATIONS IN A NUCLEIC ACID USING A HYBRIDIZATION-LIGATION PROCEDURE

[75] Inventor: Eric A. Schon, Bronx, N.Y.

[73] Assignee: The Trustees of Columbia University in the city of New York, New York, N.Y.

[21] Appl. No.: 853,000

[22] Filed: May 9, 1997

Related U.S. Application Data

[63] Continuation of Ser. No. 409,644, Mar. 24, 1995, abandoned.

[51] Int. Cl.$^6$ .............................. C12Q 1/68; C12P 19/34; C07H 21/02; C07H 21/04
[52] U.S. Cl. ................................. 435/6; 435/5; 435/91.1; 435/91.2; 435/91.3; 536/23.1; 536/24.3; 536/24.31; 536/24.33
[58] Field of Search .................................. 435/5, 6, 91.1, 435/91.2, 91.21, 91.3, 94, 91.5; 536/23.1, 24.3, 24.31, 24.32, 24.33, 24.1

[56] References Cited

U.S. PATENT DOCUMENTS 4,959,312  9/1990  Sirotkin ..................................... 435/91

FOREIGN PATENT DOCUMENTS

WO 95/22623  8/1995  WIPO .

OTHER PUBLICATIONS

Matthews, (1988), "Analytical strategies for the use of DNA probes", Anal. Biochem. 169: 1–25.

Stein et al, (1988), "Oligodeoxynucleotides as inhibitors of gene expression: a review", Cancer Research 48: 2659–2668.

Primary Examiner—W. Gary Jones
Assistant Examiner—Jeffrey Fredman
Attorney, Agent, or Firm—John P. White; Cooper & Dunham LLP

[57] ABSTRACT

The present invention provides a method for detecting a mutation in a nucleic acid molecule which comprises contacting the nucleic acid molecule with a probe. The probe comprises two covalently linked nucleic acid segments under conditions such that the unlinked end of each segment of the probe is capable of hybridizing with the nucleic acid molecule. This mixture is then contacted with a ligase under conditions such that the two hybridized probe segments will ligate and bind the nucleic acid molecule if the nucleic acid molecule contains the mutation. One would then determine the presence of bound nucleic acid molecule(s) and thereby detect the mutation in the nucleic acid molecule.

76 Claims, 3 Drawing Sheets

FIG. 1

Template: 5'-GAACAGGGTTTGTTAAGATGGCAG AGCCCGGTAATCGCATAAAACTTAA-3'
                                           G Primer: CCCAAACAATTCTACCGTC   CCGGGCCATTAGCGTATTTG
        Sequence A        5' 3'    Sequence B NNNNNNNNNNNNNNNNNNNNNNNNNNNN
                  Spacer sequence

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAACAGGGTT TGTTAAGATG GCAG        24

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGCCCGGTAA TCGCATAAAA CTTAA        25

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CTGCCATCTT AACAAACCC        19

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GTTTTATGCG ATTACCGGGC C        21

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

NNNCCCGGGN NN        12

(2) INFORMATION FOR SEQ ID NO:6:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CTGCCATCTT AACAAACCCT TTTTTTTTT TTTTTTTTT TTTTTTTTG TTTTATGCGA    60

TTACCGGGCC    70

(2) INFORMATION FOR SEQ ID NO:7:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CTGCCATCTT AACAAACCCN NNNNNNNNN NNNNNNNNN NNNNNNGTT TTATGCGATT    60

ACCGGGCC    68

METHOD TO DETECT MUTATIONS IN A NUCLEIC ACID USING A HYBRIDIZATION-LIGATION PROCEDURE

This application is a continuation of U.S. Ser. No. 08/409,644, filed Mar. 24, 1995 now abandoned.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

There is a need to improve methods to detect mutations in DNA rapidly and efficiently. The main impetus behind this need is the realization that many heritable diseases in identified genes are associated with numerous different mutations (often point mutations). For example, the genes associated with hemoglobinopathies (α- and β-globin genes) and with cystic fibrosis (a chloride transmembrane regulator gene) have now been associated with literally hundreds of documented point mutations. While in some cases such patients harbor a single, "common," mutation that is present at high frequency in the population, many patients carry the rarer mutations, which are more difficult to identify.

Previously, a typical screen for a pathogenic point mutation involves one of three approaches: (1) Single-stranded conformation polymorphism (SSCP) analysis is used to identify a gene region containing a potential polymorphic site, followed by polymerase chain reaction (PCR) and sequence analysis to identify and/or confirm the mutation.

(2) If one wants to investigate a specific mutation, the gene region can be amplified by PCR directly (without prior SSCP analysis), and the PCR product is either sequenced or subjected to restriction fragment length polymorphism (RFLP) analysis to confirm the presence of the mutation. A diagnostic method for a specific target nucleotide involving digestion of double-stranded sample nucleic acid in solution with a restriction enzyme, followed by detection of specifically sized fragments on filter paper, is discussed in U.S. Pat. No. 4,766,062 to Diamond et al. The presence of the single base substitution causative of sickle cell anemia abolishes a specific site for restriction enzyme cleavage, and thereafter two specifically sized small fragments which are usually detected are then detected in reduced amounts (for sickle cell trait) or cease to be detected (for sickle cell anemia).

(3) One can replace the RFLP analysis with the "ligase chain reaction" (LCR), in which the PCR is performed following sequence-specific ligation of two primers to each other, one of which is perfectly complementary only to the sequence containing the mutation (usually at the last [3'] nucleotide of the primer).

In all three cases, PCR is the usual starting point of the analysis, followed by analyses on gels. This work is time consuming and relatively expensive. For example, in order to assay for the presence of 100 point mutations in a given sample, one must perform 100 PCR reactions and 100 restriction digestions, followed by gel analyses. A more desirable way of assaying for the 100 mutations would be to analyze them all at once, perhaps using a "dipstick" type of test. The elimination of the LCR/PCR amplification step would also be desirable. In addition, chain reactions, e.g. LCR/PCR may present cross contamination problems.

SUMMARY OF THE INVENTION

The present invention is directed to a method for detecting a mutation in a nucleic acid molecule which comprises contacting the nucleic acid molecule with a probe. The probe may comprise two covalently linked nucleic acid segments under conditions such that the unlinked end of each segment of the probe is capable of hybridizing with the nucleic acid molecule. This mixture is then contacted with a ligase under conditions such that the two hybridized probe segments will ligate and bind the nucleic acid molecule if the nucleic acid molecule contains the mutation. One could then determine the presence of bound nucleic acid molecule(s) and thereby detect the mutation in the nucleic acid molecule.

BRIEF DESCRIPTION OF THE FIGURE

FIG. 1: Example of a sequence-specific U-shaped oligonucleotide to detect an A→G point mutation at nt-3243 in mtDNA (exemplified with SEQ ID NOS: 1–4). A region of the denatured mtDNA template is shown (5'→3'); the mutation at nt-3243 (G instead of A) is indicated in bold. The U-shaped primer (5'→3') contains a short region complementary to mtDNA sequence (vertical lines) just prior to (sequence A) and immediately following (sequence B) the mutated base, with a spacer sequence (shown) connecting them. The last base of the primer (C, in bold), is complementary to the mutated base in mtDNA (G, in bold), but not to the wild-type base (A, not bold).

DETAILED DESCRIPTION OF THE INVENTION

Figure 2:
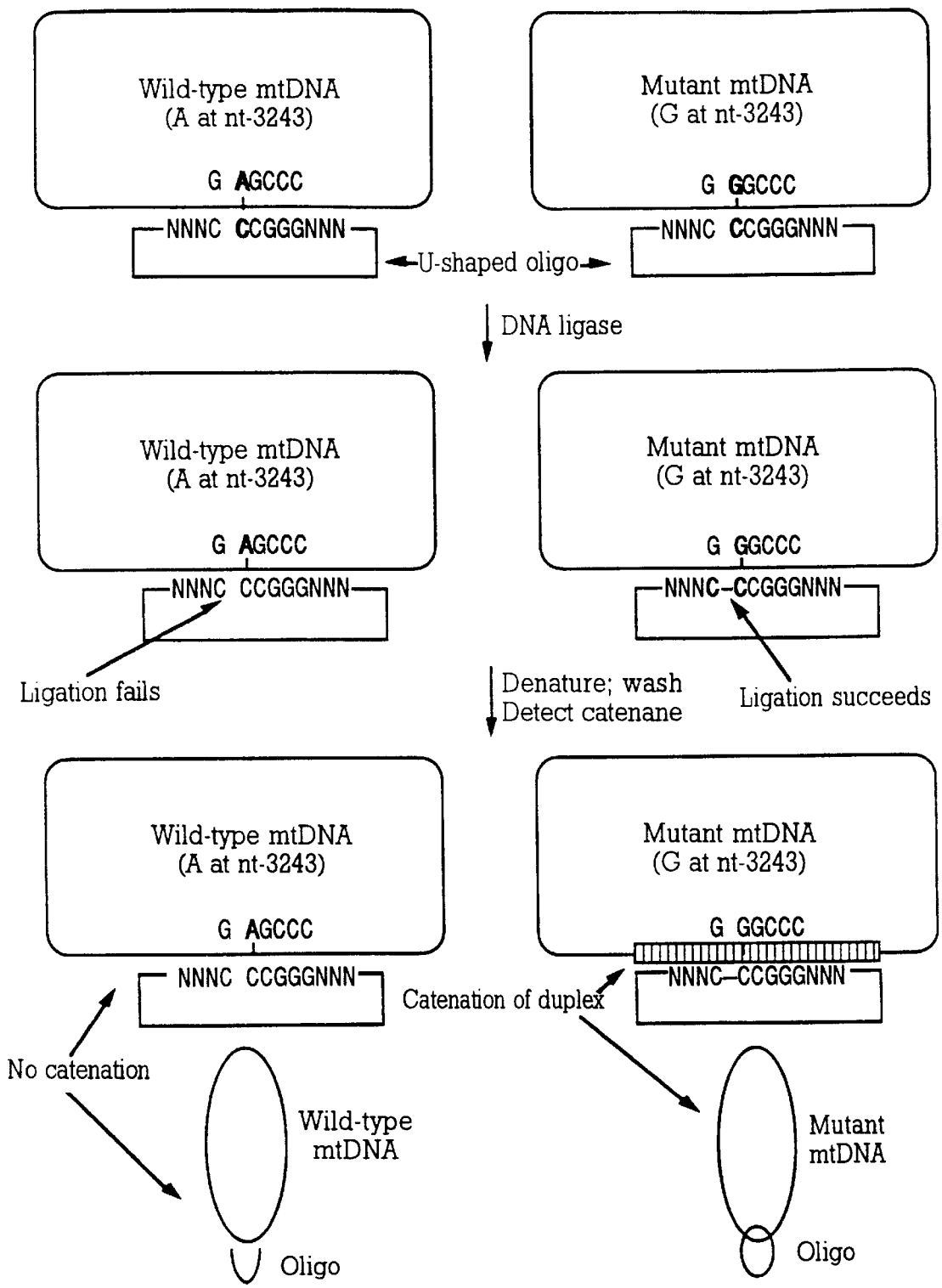
FIG. 2: Schematic description of this invention. N's denote mtDNA sequence, not random sequence as in FIG. 1. See text for description.

The present invention provides a method for detecting a mutation in a nucleic acid molecule which comprises contacting the nucleic acid molecule with a probe. The probe comprises two covalently linked nucleic acid segments under conditions such that the unlinked end of each segment of the probe is capable of hybridizing with the nucleic acid molecule. This mixture is then contacted with a ligase under conditions such that the two hybridized probe segments will ligate and bind the nucleic acid molecule if the nucleic acid molecule contains the mutation. One would then determine the presence of bound nucleic acid molecule(s) and thereby detect the mutation in the nucleic acid molecule. In addition, the method above could be applied to detect a genetic disorder or a neutral polymorphism in a subject or to select a particular mutation in a nucleic acid molecule from a population of engineered nucleic acid molecules containing random mutations.

In the method above, the nucleic acid molecule may be a DNA molecule, an RNA molecule, a mitochondrial DNA molecule, a circular DNA molecule, a chromosomal DNA molecule, a viral DNA molecule or a cDNA molecule. The nucleic acid molecule may be greater than 800 bases long or greater than 2 kilobases long.

The two covalently linked probe segments comprise nucleic acid molecules which may be modified in their sugar, phosphate or base including: phosphorothioate, phosphoramidate, phosphorodithioate, peptide nucleic acid, phosphonate, methylphosphonate or phosphate ester. Such modified nucleotides are well known to those skilled in the art, see for example, Uhlmann and Peyman, 1990.

The probe segments may also be linked together with a suitable non-nucleic acid based linker such as a polyethylene glycol, a poly-propylene glycol, a poly-phosphate linker (Benseler et al., 1993), a polypeptide linker, a poly acetic acid, a poly methacrylate, or a hydrocarbon linker which may be saturated or unsaturated, substituted or unsubstituted, polystyrene and the like. The linker should be of the appropriate length so that the two probe segments may form a loop. The optimal length of the probe segments is approximately 10–30 bases and the linker should be about two times the length of each probe segment plus 5–6 base pairs. Preferably, the probe is from about 12 to about 24 bases in length. These lengths are only approximate and other lengths have been shown to work as described herein.

The probe segments may be linked together by an oligonucleotide. The oligo need not be DNA. It can be RNA, or any synthetic molecule with the properties of "hybridizability" to the target, "ligatability," and "circularizability." An example of the latter would be a peptide-nucleic acid, or PNA (Peffer et al., 1993; Wittung et al., 1994). Similarly, the target need not be DNA, but could be RNA or any nucleic acid molecule which is capable of hybridizing with the probe segments and thus rendering it detectable by this method. The probe segments may be labeled with a detectable moiety including: a fluorescent label, a radioactive atom, a chemiluminescent label, a paramagnetic ion, biotin or a label which can be detected through a secondary enzymatic or binding step. Alternatively, the nucleic acid molecules which may contain the mutation may be labeled as above. The determination of the presence of bound nucleic acid molecule(s) may be by autoradiography, by an enzymatic reaction, by fluorescence, by chemiluminescence, or by the detection of a magnetic charge (Maniatis et al., 1989). Either the probe or the nucleic acid molecule(s) may be attached to an affinity medium. The binding of the nucleic acid molecule to the probe segments will circularize the probe segments, and if the nucleic acid molecule is circular it will make a catenane. The mutation which is detected in the above method may be a point mutation, a deletion, an insertion, a translocation, an inversion or a plurality of these.

It is generally only a specific region of the probe which binds selectively to the target nucleotide sequence. Other regions of the probe may be of various naturally occurring or synthesized sequences which do not participate in the hybridization reaction, but which may play an important role in the present invention, e.g., by serving as a site for attachment to a support or by providing some degree of separation between the support and the region to which the target nucleotide sequence binds, if desired.

The present invention provides a method to take two purified DNA plasmid templates which differ in DNA sequence at only one position, and to detect that difference utilizing a specifically designed oligonucleotide probe. The success of the method may be established by detecting the catenane (e.g. the covalently circularized oligo catenated with the circularized plasmid) on a gel. If the oligo were labeled, uncatenated free oligos would migrate off the gel and be undetected. However, label co-migrating on the gel with the plasmid would be strong proof that the oligo and the plasmid were strongly associated. Moreover, retention of this association (and of the label) following treatment to denature the oligo would then be strong evidence that the association of oligo to plasmid involved some type of binding, or based on the system, catenation as the most likely explanation.

One embodiment of this invention is to detect one of two polymorphisms, for example, a pathogenic point mutation in mitochondrial DNA (mtDNA) but not in the homologous wild-type mtDNA sequence. An oligonucleotide whose 3' end is complementary to the mutated base ("sequence B" in FIG. 1), but not to the wild-type base, will be ligated preferentially to a second oligonucleotide ("sequence A" in FIG. 1) immediately adjacent to the first sequence. Conversely, if there is a mismatch at the 3' end of sequence B, ligation to sequence A will fail. As shown in FIG. 2, if sequence A and sequence B are on the same contiguous oligonucleotide with a short "spacer" sequence between the two (e.g. 5'-A——spacer——B-3'), hybridization of the "U-shaped" oligo to a complementary mtDNA template, followed by sequence-specific ligation, will catenate the ligated oligo with the circular mtDNA. If no ligation occurs, catenation will not take place. Subsequent denaturation (e.g. by boiling or by treatment with alkali) will release all uncatenated species, but not the oligo-mtDNA catenane (see bottom section of FIG. 2). This catenane, the desired product, can then be detected by any number of "standard" methods.

The detection of mutations by the method presented herein is performed on the original DNA template, without any prior amplification step (e.g. Nikiforov et al., 1994 and Maskos and Southern, 1993). Thus, a mutation detected by this method does not require PCR. With good secondary detection methods (described herein), detection without PCR is attainable. Neither oligo nor template need to be labeled if the detection method is secondary.

One of the advantages of the invention is that it relies not on the analysis of linear pieces of DNA (usually after PCR amplification) to distinguish between two DNA sequences (e.g. wild-type and mutant), but rather upon the analysis of the interaction of a specifically-designed oligonucleotide with the sample DNA, in which the topology of the oligonucleotide DNA is changed in such a way that one can distinguish between two sample sequences. Specifically, rather than using two primers spaced widely apart (e.g. 200 bp) on the DNA as the starting point for amplification of a linear piece of DNA by PCR, the method herein uses a single linear oligonucleotide which may be both circularized and topologically catenated to the sample DNA. Importantly, this circularization can be designed to occur in a sequence-specific manner, so that two sequences can be distinguished.

The specificity of the ligation (i.e. reducing "mismatch" ligation) can be improved by various methods (position of mismatch; temperature; addition of salt or spermidine [see, for example, Wu and Wallace, 1989]). It may be preferable to use thermostable ligase (e.g. ligation at 65° C.) to reduce background. Oligos mismatched at either the first (i.e. most 5') or the last (i.e. most 3') base can be used in parallel reactions to confirm the identification of the mismatch and increase confidence of detection.

Theoretically, there is no limit to the size of the oligo to be bound. It may be a multi-kilobase-sized linearized plasmid made single-stranded by any means (e.g. denaturation; use of M13 vectors). Furthermore, the two "halves" of the oligo (sequences A and B [FIG. 1]) can be constructed separately and juxtaposed in a topologically contiguous piece of DNA later (e.g. a plasmid construct with sequences A and B attached on either side of a restriction site).

Regarding detection of the bound nucleic acid molecule

The detection step can be of either the target circle or the bound oligo. Examples of detection would include probing with template-specific DNA or with repetitive Alu sequences (in the case of human DNA). Detection could include PCR of bound templates or of bound oligos. If one wishes to label the oligo, it may be by any method; examples include labeling with a radioactive atom, fluorescent dyes (including "quenching" dyes [Lee et al., 1993]) and with avidin/biotin (see Khudyakov et al, 1994). Oligos can be synthesized with modifications (e.g. protein-nucleic acids; biotinylated or digoxigenin-labeled oligos) which can then be detected. The template DNA can be labeled by similar methods. Detection of the catenane can be by any method, including radioactive, fluorimetric, calorimetric, paramagnetic or even immunological methods (see Zhou et al., 1993).

Labeling of either the target circular oligonucleotide or the bound template can be done by incorporating nucleotides linked to a "reporter molecule." A "reporter molecule", as defined herein, is a molecule or atom which, by its chemical nature, provides an identifiable signal allowing detection of the circular oligonucleotide. Dection can be either qualitiative or quantitiative. The present invention contemplates using any commonly used reporter molecule including radionuclides, enzymes, biotins, psoralens, fluorophores, chelated heavy metals, and luciferin. The most commonly used reporter molecules are either enzymes, fluorophores or radionuclides linked to the nucleotides which are used in probe synthesis or template labeling. Commonly used enzymes include horseradish peroxidase, alkaline phosphatase, glucose oxidase and β-galactosidase, among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1,2-phenylenediamine, 5-aminosalicyclic acid or toluidine are commonly used. The probes so generated have utility in the detection of a specific DNA or RNA target in, for example, Southern analysis, Northern analysis, in situ hybridization to tissue sections or chromosomal squashes and other analytical and diagnostic procedures. The methods of using such hybridization probes are well known and some examples of such methodology are provided by Maniatis et al., 1989.

It is quite likely that the method presented herein can be used to detect mutations in single-copy genes (as are found in nuclear DNA); as alluded to above, such mutations could be detected without the necessity for PCR. Since the target DNA is relatively large, non-PCR-based detection methods, similar to those described above, could be used.

This invention is illustrated in the Experimental Detail sections which follow. These sections are set forth to aid in an understanding of the invention but are not intended to, and should not be construed to, limit in any way the invention as set forth in the claims which follow thereafter.

Experimental Details

DNA templates

As templates for this method, two PCR-amplified mtDNA sequences were subcloned. Plasmid pCR16.4 contained a 2,381-bp PCR-amplified fragment of mtDNA sequence from positions 2164–4544 (Anderson et al., 1981), including the genes specifying 16S rRNA, tRNA$^{Leu(UUR)}$, and ND1 (which are contiguous genes in the mtDNA), subcloned into the pCR™1000 vector (Invitrogen); importantly, mtDNA position 3243 within the tRNA$^{Leu(UUR)}$ gene contained an A (the wild-type sequence). Plasmid pCR16.3 was identical to plasmid pCR16.4, except for an A→G mutation at nt-3243 (the mutation also creates a new HaeIII polymorphic site). The G at nt-3243 is a pathogenic mutation in mtDNA associated with a maternally-inherited disorder known as MELAS (mitochondrial encephalomyopathy, lactic acidosis, and stroke-like episodes) (Goto et al., 1990). The presence of the A at nt-3243 in pCR16.4 and of the G at the analogous position in pCR16.3 was confirmed by DNA sequencing (not shown).

Primers

A 70-nt primer (primer LICAT-MELAS1) was synthesized, with the sequence:

5'-CTGCCATCTTAACAAACCC(T)$_{30}$GTTTTATGCGATTACCGGGCC-3'. The 19 nt at the proximal 5' end (sequence A in FIG. 1) were complementary to nt 3224–3242; the stretch of 30 T's were the spacer sequence; and the 21 nt at the distal 3' end (sequence B in FIG. 1) were complementary to nt 3243–3263. Note that the last base of the oligonucleotide (C, in bold) is complementary to the G at nt-3243 present in pCR16.3 but not to the A at nt-3243 present in pCR16.4.

The primer (approximately 40 pmoles) was labeled at the 5' end with [δ-$^{32}$P]ATP (3000 Ci/mmol; New England Nuclear) in the presence of T4 polynucleotide kinase (Boehringer Mannheim), and the end-labeled oligonuceotide was purified on a Sephadex G-25 spin column. The specific activity was about $4 \times 10^5$ cpm/mg, equivalent to about $1 \times 10^5$ cpm/pmol for LICAT-MELAS1.

A second primer (LICAT-MELAS2; 68 nt) was also synthesized, with the sequence:

5'-CTGCCATCTTAACAAACCC(N)$_{28}$GTTTTATGCGATTACCGGGCC-3', where N denotes any base.

EXAMPLE 1

Ligation-catenation

Approximately 0.5 pmoles (in 4 ml) of either plasmid pCR16.3 (MELAS; G at nt-3243) or pCRI6.4 (wild-type; A at nt-3243) were mixed with 4 ml 1N NaOH in a total volume of 20 ml containing 0.8 ml 5 mM EDTA pH 8.0, and held at room temperature for 5 min, in order to allow the double-stranded plasmid templates to denature. The denatured plasmids were then precipitated by the addition of 4 ml 10M ammonium acetate and 80 ml ethanol, centrifuged, and the pellet was lyophilized. Approximately 0.8 pmoles of labeled primer was added to the lyophilized pellet in annealing buffer (50 mM NaCl, 10 mM MgCl$_2$, 10 mM Tris-HCl pH 7.4) in a total volume of 20 ml, heated at 65° C. for 2 min, and slow-cooled over 45 min to about 35° C. Ten ml of this template/primer mixture was ligated in the presence of 1 unit T4 DNA ligase (Boehringer Mannheim) in T4 DNA ligase buffer (Boehringer Mannheim) in a total volume of 20 ml, and kept at 12°–5° C. overnight. The ligase was inactivated at 65° C., and half the mixture was treated with 0.8 ml 5 mM NaOH in a total volume of 20 ml to denature the primer. The other half was not denatured, as a control. The mixture was chilled on ice for 30 min and electrophoresed through a 0.8% agarose gel. The gel was vacuum-dried and autoradiographed at −70° C. overnight.

Results

Figure 3:
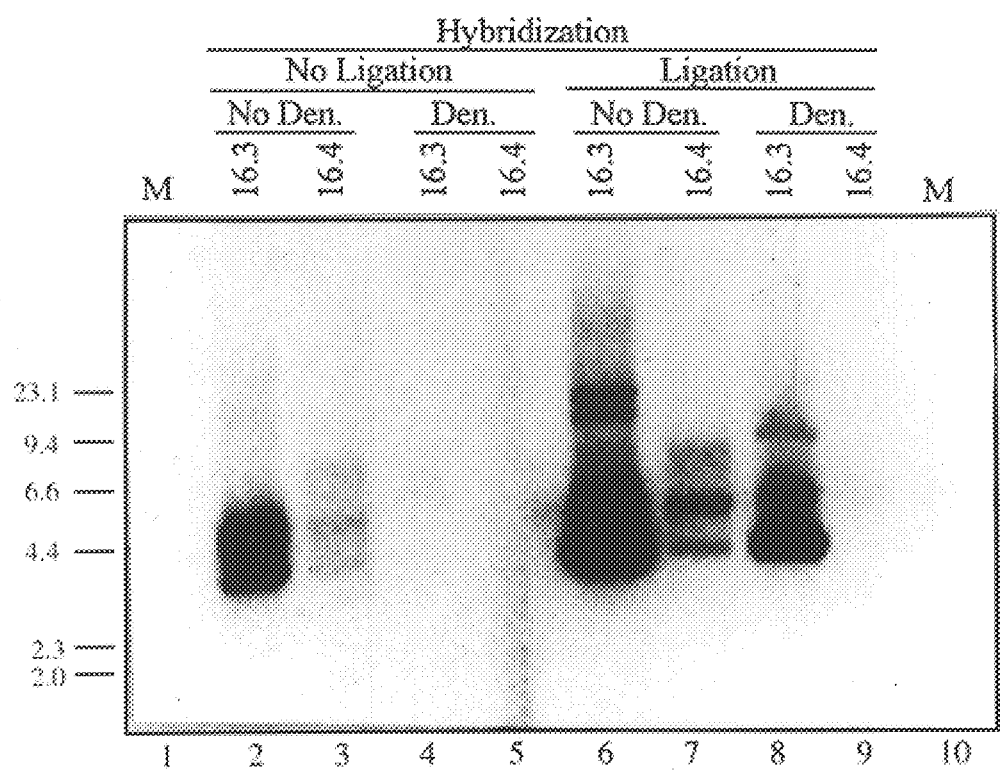
FIG. 3: Example of a successful catenation experiment. Plasmid pCR16.3 (mutant) and pCR16.4 (wild-type) were hybridized with 5'-end-labeled LICAT-MELAS1 primer, with or without ligation and denaturation (Den.). The products were electrophoresed through an agarose gel, which was then dried and subjected to autoradiography. Sizes of HindIII-digested λ markers (M) are at right, in kb. Lane numbers are at bottom.

Both plasmid pCR16.3 (containing the MELAS mutation) and plasmid pCR16.4 (wild-type) were able to hybridize with the labeled primer in the absence of ligation (FIG. 3, lanes 2 and 3, respectively). Following ligation and heat-inactivation of the ligase at 65° C., the signal from pCR16.3 was essentially undiminished, whereas the signal from pCR16.4 was severely decreased (FIG. 3, lanes 6 and 7, respectively). Following denaturation with NaOH, the signal was clearly detectable from pCR16.3, but was completely absent from pCR16.4 (FIG. 3, lanes 8 and 9, respectively).

These results indicate that the primer hybridized to both wild-type and mutant templates, as expected, and that the ligation of the mutant-specific primer was in fact specific to the mutant template. The labeled 70-nt primer should only to be visible by autoradiography in the region of the gel in which the plasmid migrates (as various topoisomers) if it is physically associated with the plasmid. Following denaturation, it is probable that this co-migration can only have occurred if the primer were covalently associated with the plasmid (i.e. a catenated pair of circles). Such catenation did not occur on the wild-type plasmid, as expected, and whatever labeled primer was not retained in the gel at the position of the plasmid must have migrated off the bottom of the gel.

Note that the denaturation of the unligated primer from the pCR16.4 template occurred both by heat treatment at 65° C. (during the ligase denaturation step) and by alkali denaturation (during the unligated-primer denaturation step). The association between the primer and template pCR16.3 survived both denaturation conditions.

This procedure utilizing the pCR16.3 probe was successful in the presence of added genomic DNA.

Discussion

Thus, these experiments demonstrate the hybridization-ligation procedure. One embodiment of this invention is the generation of topologically closed oligonucleotide circles using a second template as a "catalyst" for the closure reaction. Numerous modifications and applications immediately present themselves. A number of examples follow.

A particularly effective way to convert this invention into a dipstick test is to bind the oligo to a solid support. The U-shaped oligo can be bound covalently to a substrate (e.g. filter paper, nitrocellulose, or nylon); the target DNA is denatured in solution and hybridized to the bound oligo, followed by ligation-catenation. An example of binding is to incorporate biotin into the spacer region of the oligo, and to attach the oligo to streptavidin-treated paper (like a "lollypop"). Denaturation following ligation will release all uncatenated template species from the paper into the solution (where they can be washed away), but the sequence-specific oligo-mtDNA catenane will stay stuck to the paper. This catenane—the desired product—can then be detected by "standard" methods.

Covalent linkage of the oligo to the substrate can be by any method, but is preferably a linkage through the "spacer" bases of the oligo, not through modification of the 5' or 3' ends, which would likely interfere with the ligation step (Gingeras et al., 1987). End-modification would not be precluded, however, as long as the ligation-catenation of the desired target could still proceed.

Note that if one placed 100 "dots" of 100 different mutation-specific oligos on the paper, and challenged the paper with sample DNA (presumably containing only one of the 100 possible mutations), only one of the 100 dots would test positive following this method. This is a dipstick test. Maskos and Southern (1993) describe a method for the parallel analysis of multiple mutations in multiple samples.

With suitable control dots, one could even quantitate the extent of reaction (e.g. count how much mutated DNA was present) (Kohsaka, et al., 1993). Homozygous, heterozygous, hemizygous, and even compound heterozygous genotypes could be distinguished, based on the pattern and number of "signaling" dots. Cancers with "reductions to homozygosity" might also be detectable, as would be regions of amplified DNA (e.g. "heterogeneously staining regions" after amplification of dihydrofolate reductase genes following methotrexate treatment).

This procedure could be performed in solution, but the desired catenated species could be "captured" in any number of ways (e.g. on gels [as was done in the initial reduction to practice] or on columns or supports, by affinity capture) (Blanks and Mclaughlin, 1988 and Gingeras et al., 1987).

Instead of binding the oligo to a substrate and adding template DNA in solution, one can do the reverse: bind the template to a surface and add the oligo in solution. This application would be extremely useful in in-situ hybridization (ISH) to detect point mutations. Currently, ISH for point mutations requires "allele-specific oligonucleotides" that hybridize based on slight differences in melting temperatures between wild-type and mutant targets. ASO's for ISH are rarely used, because it an extremely tricky and time-consuming method with high backgrounds. If the ISH probe were a [labeled] oligo probe as described here, it would catenate preferentially to one of the two sequences with no necessity to work out annealing conditions. This idea is currently being tested to detect mtDNA point mutations in muscle sections. A variant of this is ISH to detect point mutations in chromosomal DNA.

As described above, the target need not be a circle. Because the circularized oligo is small (less than 100 nt) and the target is so big (16.6 kb for mtDNA), a large linear DNA (e.g. undigested or restriction-digested or sonicated nuclear DNA) is not likely to "slip through" the ligated oligo. Moreover, the intramolecular secondary structure of the single-stranded target will also inhibit "slip-through." Even if a target circle were necessary however, one could circularize restriction-digested nuclear DNA by intramolecular ligation at low concentration (perhaps even while the oligo ligation step proceeds).

This method could detect not only point mutations, but large-scale DNA rearrangements (e.g. deletions, inversions, translocations) as well. An example would be the "Philadelphia" chromosomal translocation associated with chronic myelogenous leukemia.

REFERENCES

Anderson, S., Bankier, A. T., Barrell, B. G., de Bruijn, M. H. L., Coulson, A. R., Drouin, J., Eperon, I. C., Nierlich, D. P., Roe, B. A., Sanger, F., Schreier, P. H., Smith, A. J. H., Staden, R. and Young, I. G. (1981). Sequence and organization of the human mitochondrial genome. Nature 290, 457–465.

Benseler, F., Fu, D., Ludwig, J. and McLaughlin, L. W. (1993). Hammerhead-like molecule containing non-nucleoside linkers are active RNA catalysts. J. Am. Chem. Soc. 115: 8483–84.

Blanks, R. and McLaughlin, L. W. (1988) An oligodeoxynucleotide affinity column for the isolation of sequence specific DNA binding proteins. Nucl. Acids Res. 16: 10283–10299.

Diamond S. E., Brewen, J. G., Williams, J. I., Ellwood, M. S., Collins, M., and Fritsch, E. F. U.S. Pat. No. 4,766,062; filed May 7, 1984, issued Aug. 23, 1988.

Gingeras, T. R., Kwoh, D. Y. and Davis, G. R. (1987) Hybridization properties of immobilized nucleic acids. Nucl. Acid Res. 15: 5373–5390.

Goto, Y. -i., Nonaka, I. and Horai, S. (1990). A mutation in the tRNA$^{Leu(UUR)}$ gene associated with the MELAS subgroup of mitochondrial encephalomyopathies. Nature 348, 651–653.

Khudyakov, Y. E., Gaur, L., Singh, J., Patel, P. and Fields, H. A. (1994). Primer specific solid-phase detection of PCR products. Nucl. Acids Res. 22, 1320–1321.

Kohsaka, H., Taniguchi, A., Richman, D. D. and Carson, D. A. (1993) Microtiter format gene quantification by covalent capture of competitive PCR products: application to HIV-1 detection. Nucl. Acids Res. 21, 3469–3472.

Kool, E. T. PCT International Publication No. WO 92/17484; filed 26 Mar. 1992.

Lee, L. G., Connell, C. R. and Bloch, W. (1993). Allelic discrimination by nick-translation PCR with fluorogenic probes. Nucl. Acids Res. 21, 3761–3766.

Maniatis, T., Fritsch, E. and Sambrook, J. (1989). *Molecular Cloning: A Laboratory Manual*. Second Edition. Cold Spring Harbor, N.Y.: Cold Spring Harbor Laboratory Press.

Maskos, U. and Southern E. M. (1993) A novel method for the parallel analysis of multiple mutations in multiple samples. Nucl. Acids Res. 21, 2269–2270.

Nikiforov, T. T., Rendle, R. B., Goelet, P., Rogers, Y., Kotewicz, M. L., Anderson, S., Trainor, G. L. and Knapp, M. R. (1994) Genetic Bit Analysis: a solid phase method for typing single nucleotide polymorphisms. Nucl. Acids Res. 22: 4167–4175.

Peffer, N. J., Hanvey, J. C., Bisi, J. E., Thomson, S. A., Hassman, C. F., Noble, S. A. and Babiss, L. E. (1993). Strand-invasion of duplex DNA by peptide nucleic acid oligomers. Proc. Natl. Acad. Sci. USA 90, 10648–10652.

Uhlmann, E. and Peyman, A. (1990). Antisense Oligonucleotides: A New Therapeutic Principle. Chemical Reviews 90: 544–584.

Wittung, P., Nielsen, P. E., Buchardt, O., Egholm, M. and Norden, B. (1994). DNA-like double helix formed by peptide nucleic acid. Nature 368, 561–563.

Wu, D. Y. and Wallace, R. B. (1989). Specificity of the nick-closing activity of bacteriophage T4 DNA ligase. Gene 76, 245–254.

Zhou, H., Fisher, R. J. and Papas, T. S. (1993). Universal immuno-PCR for ultra-sensitive target protein detection. Nucl. Acids Res. 21, 6038–6039.

What is claimed is:

1. A method for detecting the presence or absence of a mutation characterized by the presence of a predefined nucleotide at a predefined position in a nucleic acid molecule which comprises:

(a) contacting the nucleic acid molecule with a probe comprising a first and a second nucleic acid segment, the 5' end of the first segment being covalently linked to the 3' end of the second segment, wherein either (a) the nucleotide at the 5' end of such second segment is complementary to the predefined nucleotide or (b) the nucleotide at the 3' end of such first segment is complementary to the predefined nucleotide, under conditions such that the probe hybridizes with the nucleic acid molecule;

(b) contacting the hybridized product from step (a) with a ligase under conditions such that the unlinked ends of the segments ligate together if the nucleic acid molecule contains the mutation, and (c) determining whether the unlinked ends of the segments have ligated together, so as to thereby detect the presence or absence of the mutation in the nucleic acid molecule with the proviso that when the nucleic acid molecule is linear, it is greater than 800 bases in length.

2. The method of claim 1, wherein the nucleic acid molecule is a DNA molecule.

3. The method of claim 1, wherein the nucleic acid molecule is an RNA molecule.

4. The method of claim 1, wherein the nucleic acid molecule is a mitochondrial DNA molecule.

5. The method of claim 1, wherein the nucleic acid molecule is a chromosomal DNA molecule.

6. The method of claim 1, wherein the nucleic acid molecule is a viral DNA molecule.

7. The method of claim 1, wherein the nucleic acid molecule is a cDNA molecule.

8. The method of claim 1, wherein the nucleic acid molecule is greater than 800 bases long.

9. The method of claim 1, wherein the nucleic acid molecule is greater than 2 kilobases long.

10. The method of claim 1, wherein the probe segments comprise nucleotides modified in their sugar, phosphate or base.

11. The method of claim 10, wherein the modified nucleotide is a phosphorothioate, phosphoramidate, phosphorodithioate, peptide nucleic acid, phosphonate, methylphosphonate or phosphate ester.

12. The method of claim 1, wherein the two probe segments are covalently linked by an oligonucleotide.

13. The method of claim 1, wherein the probe is labeled with a detectable moiety.

14. The method of claim 13, wherein the detectable moiety is a florescent label, a radioactive atom, a chemiluminescent label, a paramagnetic ion, biotin or a label which can be detected through a secondary enzymatic or binding step.

15. The method of claim 1, wherein the determination is by means of an enzymatic reaction selection method.

16. The method of claim 1, wherein the determination is by means of a fluorescence selection method.

17. The method of claim 1, wherein the determination is by means of a chemiluminescence selection method.

18. The method of claim 1, wherein the determination is by means of a magnetic charge selection method.

19. The method of claim 1, wherein the probe is attached to a solid support.

20. The method of claim 1, wherein the nucleic acid molecules are attached to a solid support.

21. The method of claim 1, wherein the nucleic acid molecule is circular and ligation of the unlinked ends results in catenation.

22. The method of claim 1, wherein the mutation(s) is a point mutation.

23. The method of claim 1, wherein the mutation(s) is a deletion mutation.

24. The method of claim 1, wherein the mutation(s) is an insertion mutation.

25. The method of claim 1, wherein the mutation(s) is a translocation mutation.

26. The method of claim 1, wherein the mutation(s) is an inversion mutation.

27. The method of claim 1, wherein the nucleic acid molecule contains a plurality of detectable mutations.

28. A method for detecting the presence or absence of a predefined mutation characterized by the presence of a predefined nucleotide at a predefined position in a nucleic acid molecule associated with a genetic disorder in a subject which comprises:

(a) contacting a sample of bodily fluid or tissue from the subject containing the nucleic acid molecule associated with the genetic disorder, with a probe comprising a first and a second nucleic acid segment, the 5' end of the first segment being covalently linked to the 3' end of the second segment, wherein either (a) the nucleotide at the 5' end of such second segment is complementary to the predefined nucleotide or (b) the nucleotide at the 3' end of such first segment is complementary to the predefined nucleotide, under conditions such that the probe hybridizes with the nucleic acid molecule;

(b) contacting the hybridized product from step (a) with a ligase under conditions such that the unlinked ends of the segments ligate together if the nucleic acid molecule contains the predefined mutation associated with the genetic disorder, and (c) determining whether the unlinked ends of the segments have ligated together, so as to thereby detect the presence or absence of the predefined mutation associated with the genetic disorder in the subject with the proviso that when the nucleic acid molecule is linear, it is greater than 800 bases in length.

29. The method of claim 28, wherein the nucleic acid molecule(s) is covalently linked to a solid support.

30. The method of claim 28, wherein the probe(s) is covalently linked to a solid support.

31. The method of claim 28 or 29, wherein the solid support is a microscope slide comprised of plastic or glass, either uncoated or coated with a suitable attachment substrate.

32. The method of claim 28 or 29, wherein the solid support is a nylon membrane, a cellulose acetate membrane, an epoxy-activated synthetic copolymer membrane or a nitrocellulose membrane.

33. The method of claim 28, wherein the solid support is a tube or bead or any part thereof, which is sepharose, latex, glass or plastic.

34. The method of claim 28, wherein the probe is labeled with a detectable moiety.

35. The method of claim 34, wherein the detectable moiety is a fluorescent label, a radioactive atom, a chemiluminescent label, a paramagnetic ion, biotin or a label which can be detected through a secondary enzymatic or binding step.

36. The method of claim 28, wherein the determination is by means of an enzymatic reaction selection method.

37. The method of claim 28, wherein the determination is by means of a fluorescence selection method.

38. The method of claim 28, wherein the determination is by means of a chemiluminescence selection method.

39. The method of claim 28, wherein the determination of the presence or absence of bound nucleic acid molecule(s) is by means of a magnetic charge selection method.

40. The method of claim 28, wherein the nucleic acid molecules are attached to a solid support.

41. The method of claim 28, wherein the nucleic acid molecule is circular and ligation of the unlinked ends results in catenation.

42. The method of claim 28, wherein the genetic disorder is associated with a point mutation.

43. The method of claim 28, wherein the genetic disorder is associated with a deletion mutation.

44. The method of claim 28, wherein the genetic disorder is associated with an insertion mutation.

45. The method of claim 28, wherein the genetic disorder is associated with a translocation mutation.

46. The method of claim 28, wherein the genetic disorder is associated with an inversion mutation.

47. The method of claim 28, wherein the nucleic acid molecule contains a plurality of detectable genetic disorders.

48. A method for identifying the presence or absence of a predefined neutral polymorphism characterized by the presence of a predefined nucleotide at a predefined position in a nucleic acid molecule in a subject which comprises:

(a) contacting a sample of bodily fluid or tissue from the subject containing the nucleic acid molecule associated with the neutral polymorphism, with a probe comprising a first and a second nucleic acid segment, the 5' end of the first segment being covalently linked to the 3' end of the second segment, wherein either (a) the nucleotide at the 5' end of such second segment is complementary to the predefined nucleotide or (b) the 3' end of such first segment is complementary to the predefined nucleotide, under conditions such that the probe hybridizes with the nucleic acid molecule;

(b) contacting the hybridized product from step (a) with a ligase under conditions such that the unlinked ends of the segments ligate together if the nucleic acid molecule contains the neutral polymorphism, and (c) determining whether the unlinked ends of the segments have ligated together, so as to identify the presence or absence of the predefined neutral polymorphism in the subject with the proviso that when the nucleic acid molecule is linear, it is greater than 800 bases in length.

49. A method for selecting a particular mutation in a nucleic acid molecule from a population of engineered nucleic acid molecules containing random mutations, which comprises:

(a) contacting a sample containing the nucleic acid molecule which may contain the particular mutation, with a probe comprising a first and a second nucleic acid segment, the 5' end of the first segment being covalently linked to the 3' end of the second segment, wherein either (a) the nucleotide at the 5' end of such second segment is complementary to the predefined nucleotide or (b) the nucleotide at the 3' end of such first segment is complementary to the predefined nucleotide, under conditions such that the probe hybridizes with the nucleic acid molecule;

(b) contacting the hybridized product from step (a) with a ligase under conditions such that the unlinked ends of the segments ligate together if the nucleic acid molecule contains the particular mutation, and (c) determining whether the unlinked ends of the segments have ligated together, so as to thereby select the nucleic acid molecule containing the particular mutation from the population of engineered nucleic acid molecules with the proviso that when the nucleic acid molecule is linear, it is greater than 800 bases in length.

50. The method of claim 49, wherein the nucleic acid molecule is covalently linked to a solid support.

51. The method of claim 49, wherein the probe is covalently linked to a solid support.

52. The method of claim 49, wherein the solid support is a microscope slide comprised of plastic or glass.

53. The method of claim 49, wherein the solid support is a nylon or nitrocellulose membrane.

54. The method of claim 49, wherein the solid support is a bead which is sepharose, latex, glass or plastic.

55. The method of claim 49, wherein the probe is labeled with a detectable moiety.

56. The method of claim 55, wherein the detectable moiety is a florescent label, a radioactive atom, a chemiluminescent label, a paramagnetic ion, biotin or a label which can be detected through a secondary enzymatic or binding step.

57. The method of claim 49, wherein the selection is by means of an enzymatic reaction selection method.

58. The method of claim 49, wherein the selection is by means of a fluorescence based selection method.

59. The method of claim 49, wherein the selection is by means of a chemiluminescence based selection method.

60. The method of claim 49, wherein the selection is by means of magnetic charge based selection method.

61. The method of claim 49, wherein the nucleic acid molecules are attached to a solid support.

62. The method of claim 49, wherein the nucleic acid is circular and ligation of the unlinked ends results in catenation.

63. The method of claim 49, wherein the particular mutation is associated with a point mutation.

64. The method of claim 49, wherein the particular mutation is associated with a deletion mutation.

65. The method of claim 49, wherein the particular mutation is associated with an insertion mutation.

66. The method of claim 49, wherein the particular mutation is associated with an inversion mutation.

67. A method for detecting the presence or absence of a mutation characterized by the presence of a predefined nucleotide at a predefined position in a circular DNA molecule which comprises:

(a) contacting the circular DNA molecule with a probe comprising a first and a second nucleic acid segment, the 5' end of the first segment being covalently connected to the 3' end of the second segment, wherein the 5' end of the second segment or the 3' end of the first segment is complementary to the predefined nucleotide, under conditions such that the probe hybridizes with the circular DNA molecule;

(b) contacting the hybridization product from step (a) with a ligase under conditions such that the unlinked ends of the first and second segments ligate together only if the circular DNA molecule contains the predefined nucleotide mutation, and (c) determining whether the unlinked ends of the first and second segments have ligated together, so as to thereby detect the presence or absence of the mutation in the circular DNA molecule.

68. The method of claim 67, wherein the covalent connection of the probe ends is performed by enzymatic ligation.

69. The method of claim 67, wherein the target molecule is a cDNA or an RNA sequence.

70. The method of claim 67, wherein the probe is an oligonucleotide.

71. The method of claim 67, wherein the segment or segments are selected from polypeptide, hydrocarbon linker, poly-propylene glycol, or poly-phosphate linker.

72. The method of claim 67, wherein the probe or probes are immobilized to a solid support.

73. The method of claim 67, wherein the target sequence is immobilized to a solid support.

74. The method of claim 67, wherein the sample is a population of engineered nucleic acid molecules.

75. A method of detecting a target molecule having a defined nucleic acid sequence in a sample which comprises:

(a) providing a detectable probe with two free nucleic acid end parts which are complementary to at least a part of, and capable of hybridizing to, two regions of the target molecule, (b) hybridizing the probe ends to the target molecule under hybridizing conditions, (c) covalently connecting the ends of the hybridized probe with each other to form a circularized structure which binds the target molecule through catenation, (d) subjecting the target molecule to denaturing conditions to release any non-circularized probe from the target molecule, thereby retaining only the circularized probe bound to the target molecule, (e) detecting the presence of catenated probe, as indicative of the presence of the target molecule of defined nucleic acid sequence thus detecting the target nucleic acid in the sample, with the proviso that when the target molecule is linear, it is greater than 800 bases in length.

76. A method of selectively capturing a target molecule having a defined nucleic acid sequence on a solid support which comprises:

(a) providing a probe with two free nucleic acid end parts which are complementary to at least a part of and capable of hybridizing to two regions of the target molecule, said probe being immobilized to the solid support, (b) hybridizing the probe ends to the target molecule under hybridizing conditions, (c) covalently connecting the ends of the hybridized probe with each other to form a circularized structure which binds with the target molecule through catenation, (d) subjecting the support with the captured target molecule to denaturing conditions to release any non-catenated target molecule from the support so as to selectively capture a target molecule with a defined nucleic acid sequence, with the proviso that when the target molecule is linear, it is greater than 800 bases in length.

* * * * *

UNITED STATES PATENT AND TRADEMARK OFFICE
CERTIFICATE OF CORRECTION

PATENT NO. : 5,866,337
DATED : February 2, 1999
INVENTOR(S) : Eric A. Schon

It is certified that error appears in the above-indentified patent and that said Letters Patent is hereby corrected as shown below:

Title page: change the filing date from "May 9, 1997" to --May 8, 1997--

Signed and Sealed this

Twelfth Day of October, 1999

Attest:

Q. TODD DICKINSON

*Attesting Officer*  *Acting Commissioner of Patents and Trademarks*